(12) United States Patent
Donderici et al.

(10) Patent No.: US 10,088,593 B2
(45) Date of Patent: Oct. 2, 2018

(54) IMPEDANCE ANALYSIS FOR FLUID DISCRIMINATION AND MONITORING

(71) Applicant: Halliburton Energy Services, Inc., Houston, TX (US)

(72) Inventors: Burkay Donderici, Houston, TX (US); Glenn A. Wilson, Singapore (SG); Ahmed E. Fouda, Houston, TX (US)

(73) Assignee: HALLIBURTON ENERGY SERVICES, INC., Houston, TX (US)

( * ) Notice: Subject to any disclaimer, the term of this patent is extended or adjusted under 35 U.S.C. 154(b) by 0 days.

(21) Appl. No.: 15/126,534

(22) PCT Filed: Jun. 23, 2014

(86) PCT No.: PCT/US2014/043705
§ 371 (c)(1),
(2) Date: Sep. 15, 2016

(87) PCT Pub. No.: WO2015/199648
PCT Pub. Date: Dec. 30, 2015

(65) Prior Publication Data
US 2017/0090060 A1 Mar. 30, 2017

(51) Int. Cl.
*G01V 3/24* (2006.01)
*E21B 47/00* (2012.01)
(Continued)

(52) U.S. Cl.
CPC ............ *G01V 3/24* (2013.01); *E21B 47/0005* (2013.01); *E21B 49/08* (2013.01); *G01N 27/02* (2013.01); *E21B 33/14* (2013.01)

(58) Field of Classification Search
CPC .......... E21B 49/08; E21B 33/14; E21B 47/00; E21B 47/0005; G01N 27/02; G01V 3/24
(Continued)

(56) References Cited

U.S. PATENT DOCUMENTS 4,122,387 A * 10/1978 Ajam ..................... G01V 3/24
324/375
7,256,582 B2   8/2007 Gorek et al.
(Continued)

FOREIGN PATENT DOCUMENTS

WO   WO-2007123802 A2   11/2007
WO   WO-2015199648 A1   12/2015

OTHER PUBLICATIONS

"International Application Serial No. PCT/US2014/043705, International Search Report dated Apr. 10, 2015", 4 pgs.
(Continued)

*Primary Examiner* — Jay Patidar
(74) *Attorney, Agent, or Firm* — Chamberlain Hrdlicka (57) ABSTRACT

An apparatus and method may operate to mount one or more communication assemblies relative to the exterior of a casing being placed in a borehole. Each communication assembly is configured to cause electrodes of a fluid sensing assembly to inject currents into fluids in one or more regions of the annulus surrounding the casing, and to obtain excitation responses from electrodes of the fluid sensing assembly, where the excitation responses vary based on electrical properties of fluids in one or more regions of the annulus surrounding the casing. Control is provided to control which electrodes of the fluid sensing assembly will inject currents and generate excitation responses and to control which electrodes of the fluid sensing assembly will sense the currents. Additional apparatus, systems, and methods are disclosed.

20 Claims, 9 Drawing Sheets (51) Int. Cl.
*E21B 49/08* (2006.01)
*G01N 27/02* (2006.01)
*E21B 33/14* (2006.01)

(58) Field of Classification Search
USPC .......................................................... 324/324
See application file for complete search history.

(56) References Cited

U.S. PATENT DOCUMENTS

| | | |
|---|---|---|
| 7,679,368 B2 | 3/2010 | Folberth |
| 8,390,295 B2 * | 3/2013 | Gorek ..................... G01V 3/20 |
| | | 166/254.1 |
| 8,584,519 B2 | 11/2013 | Maida et al. |
| 2013/0088364 A1 | 4/2013 | Bittar et al. |

OTHER PUBLICATIONS

"International Application Serial No. PCT/US2014/043705, Written Opinion dated Apr. 10, 2015", 10 pgs.
"Venezuela Application Serial No. 2015-000480, Office Action dated Jun. 22, 2016".

* cited by examiner

IMPEDANCE ANALYSIS FOR FLUID DISCRIMINATION AND MONITORING

PRIORITY APPLICATIONS

This application is a U.S. National Stage Filing under 35 U.S.C. § 371 from International Application No. PCT/US2014/043705, filed on Jun. 23, 2014, and published as WO 2015/199648 A1 on Dec. 30, 2015, which application and publication are incorporated herein by reference in their its entirety.

BACKGROUND

Understanding the structure and properties of geological formations is important for a wide variety of applications in well and reservoir management, monitoring, and remediation. Fluid sensing devices can detect certain properties of fluids to aid in attaining this understanding. However, available fluid sensing devices typically couple to a wireline tool or to a drill string or drill string tool such as a logging-while-drilling (LWD) tool and, as such, are isolated from annular regions between a casing string and formation. Therefore, available fluid sensing devices cannot detect many conditions that would be of interest to an operator during or after cementation processes when operators place cement in the annular regions. Some available fluid sensing devices may also be incapable of detecting the presence of low amounts of oil-based muds or other undesirable fluids in the annular region.

DETAILED DESCRIPTION

To address some of the challenges described above, as well as others, apparatuses, systems, and methods are described herein for using electrode-based fluid sensing components, mounted on a casing, to detect identities or properties of fluids in an annulus between the casing and a formation.

Figure 1:
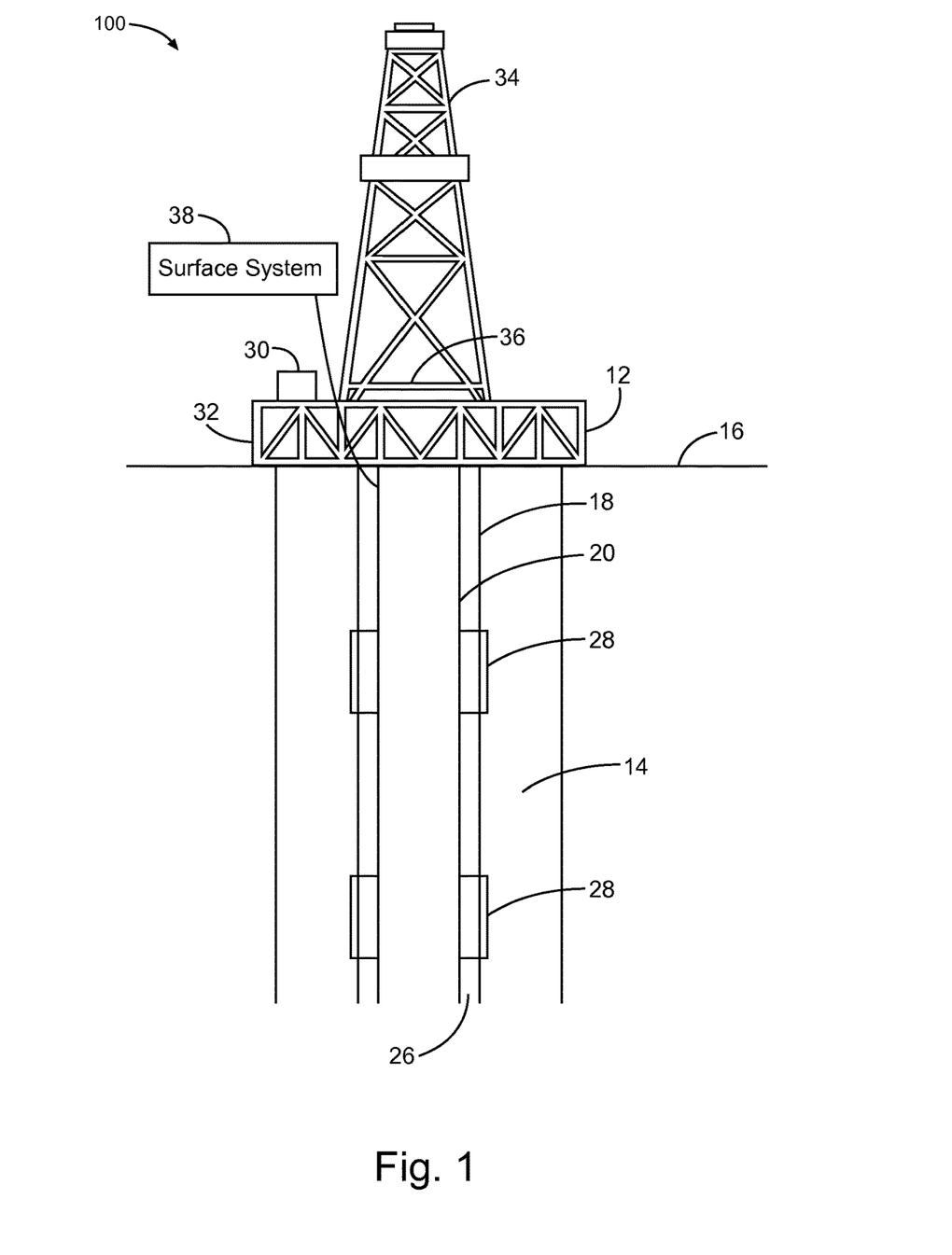
FIG. 1 illustrates a system in which example embodiments can be implemented.

FIG. 1 illustrates a drilling system 100 in which example embodiments can be implemented. Drilling system 100 includes a drilling rig 12 centered over a subterranean oil or gas-bearing formation 14 located below the earth's surface 16. Rig 12 includes a derrick 34 supporting a hoisting apparatus 36 for raising and lowering pipe strings such as casing 20, and other equipment into a wellbore 18. One or more pumps 30 are arranged for pumping of a variety of wellbore fluids as may be used for various well operations (e.g., drilling mud, well control fluids, and cement or other sealants, etc.).

Wellbore 18 has been drilled through the various earth strata, including formation 14. While wellbore 18 is shown as being drilled vertically, wellbore 18 can also be drilled horizontally. During well completion, casing 20 is placed in wellbore 18 to stabilize the well and to facilitate the production of oil and gas from formation 14. The casing 20 together with the formation sidewalls defining wellbore 18 define an annulus 26 surrounding the casing Drilling mud or other fluids can initially be in place in annulus 26 to maintain pressure control of the well. "Cement" or another form of sealant is used to secure casing 20 in place and to isolate the formations penetrated by wellbore 18 from one another. In an example cementation process, cement slurry is pumped down the inside of casing 20. As the cement slurry reaches the bottom of casing 20, the cement slurry flows out of casing 20 and up through the annulus, displacing any fluid such as drilling mud in annulus 26. During spotting of the cement slurry, the cement can become contaminated with drilling mud or other fluids, and this contamination can have a negative impact on the curing and integrity of the cement.

In various example systems, different structures and methodologies are used to measure the electrical impedance of fluids in annulus 26 between casing 20 and formation 14 to identify, or at least infer, the electrical environment in the surrounding annulus 26. As emplaced cement cures, chemical reactions and changes in cement structure result in changes in measured impedance, and thereby surface system 38 or another processor can monitor the cure state and quality of cement in response to the changes in impedance measurements. Further, surface system 38 or another processor can perform fluid identification through impedance measurements. In embodiments, EM fluid sensor systems 28 can transmit, receive, process, and communicate EM signals to a central processing unit, for example surface system 38, located at the wellhead.

Figure 2:
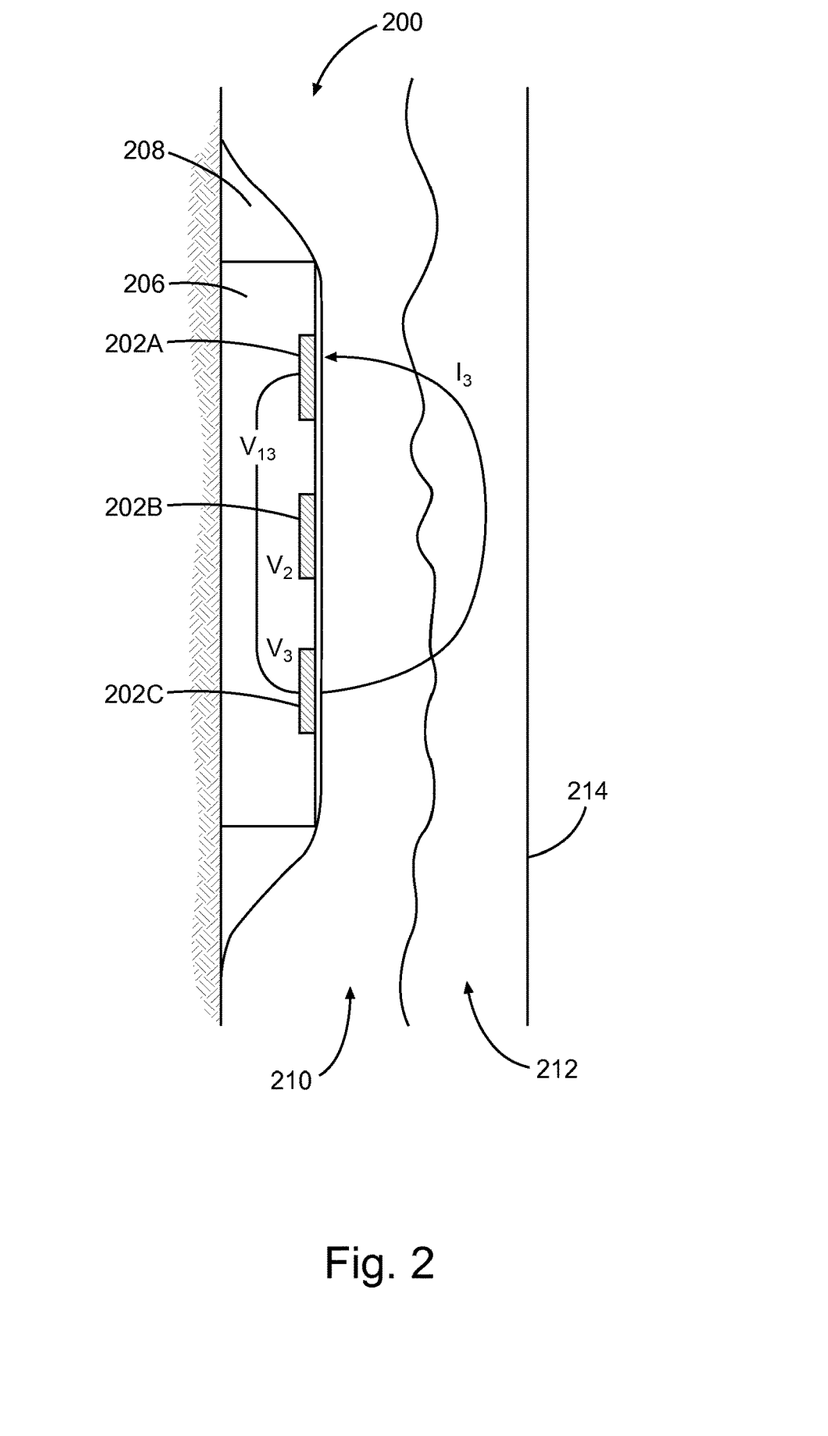
FIG. 2 depicts a side view of an example fluid sensing component as can be used to measure the sealant present within an annulus by measuring electrical impedance in accordance with some embodiments.

FIG. 2 depicts a side view of an example fluid sensing component 200 as can be used to measure the cement (or other well-servicing fluid(s)) present within annulus 26 by measuring electrical impedance in accordance with some embodiments. Fluid sensing component 200 includes electrodes 202A, 202B and 202C mounted on an insulating base 206 to prevent shorts against metallic surfaces, such as the body member of a communication assembly (as described below, referring to FIGS. 7, 8, and 9A-G) or a supporting section of casing 20. A material such as Protech DRB™ or Protech CRB™, available from the Halliburton Company of Houston, Tex. can provide a suitable insulating base 206. Some fluid sensing components 200 can include more or fewer than three electrodes 202A-C, and electrodes 202A-C can be in other configurations, for example including those as described herein in reference to FIGS. 8 and 9A-G.

A protective layer 208 may be disposed over electrodes 202A-C to insulate them from well fluids and to provide abrasive resistance for electrodes 202A-C. This barrier may include a ceramic or epoxy resin. In the depicted example, electrodes 202A-C are not in direct contact with the fluids by virtue of protective layer 208. In at least these embodiments, electrodes 202A-C may couple capacitively with the fluids in the annulus.

One or more of the electrodes 202A-C (for example electrode 202C, e.g., the "survey electrode"), can receive excitation signals and can thus inject current into the surrounding environment, such as into cement 210 (as an example fluid). The injected current can then return in one or more of the other electrodes 202B-C. A processor or other system, for example, surface system 38, or another processor can calculate impedance of the surrounding environment as described herein using measurements of voltage or current induced at one or more electrodes 202A-C.

In some situations, undesired fluids or other contaminants enter or travel in the annulus. As one example, during times of cement emplacement, another fluid, such as drilling mud can remain in the annulus, rather than being displaced by the cement slurry, as indicated in FIG. 2. It should be understood that the depiction in FIG. 2 is presented for clarity of illustration, and is not intended to be representative of an actual placement or distribution of cement versus drilling mud. As one example, such drilling mud might be an oil-based mud 212, which will typically be more resistive than cement 210. Presence of the oil-based mud is significant because, depending on the location of the drilling mud, it may indicate a cementing operation that is not proceeding as intended. Unless injection currents traverse the annulus sufficiently to traverse oil-based mud 212, impedance measurements will not be sensitive to the presence of the oil-mud, and would thus fail to identify the undesired drilling mud presence.

Some embodiments provide enhanced sensitivity of impedance measurements. In some embodiments, injection currents will beneficially be focused, to achieve greater depth of penetration across the dimension of the annulus, and in some cases into the surrounding formations. Such focused current injection systems can be implemented to lengthen the path that the injected current must traverse to reach a return electrode, and can thereby cause the injected current to traverse fluids that might otherwise be missed. In some cases, the focusing may be implemented in a manner to cause the injected current to traverse paths of varying distances from survey electrode 202C to a return electrode 202A. Once signals resulting from the injected currents that have traversed a path in the annulus (and potentially the formation) are received at a return electrode, measurement of potential (i.e., voltage) differences between the injection and return electrodes facilitates the determining of the impedance of the material(s) in the path traversed by the current.

In the specific example system of FIG. 2, survey electrode 202C will receive an excitation signal and inject current $I_3$ into the surrounding environment. In this example, the same excitation signal will be provided to electrode 202B (e.g., the "focusing electrode"), except that the excitation signals will be modified by current limiter circuitry (not shown in FIG. 2), to prevent substantial current from flowing from the focusing electrode 202B. The current limited signal at the focusing electrode 202B, which matches the signal at the survey electrode 202C, forces injection current $I_3$ injected at the survey electrode 202C to traverse the surrounding environment, including cement 210 and oil-based mud 212, to reach at least the return electrode 202A. In some embodiments, injection current $I_3$ can also pass into the surrounding formation 214. It will be understood by those skilled in the art that the depicted relative widths or thicknesses of column 212 and cement 210 is not an accurately-scaled representation, and that the width or thickness of column 212 will typically be much less than the width or thickness of cement 210. The relative widths and thicknesses, shown in FIG. 2, are intended for illustrative purposes only, to aid in describing the capability of various embodiments to perform impedance measurements beyond cement or other materials to help detect oil-based mud or other fluids that may be present downhole or for detecting voids in fluids or in the formation.

Control circuitry can measure the potential difference between the return electrode 202A and the survey electrode 202C (i.e., voltage $V_{1-3}$) to calculate impedance $Z_{1-3}$ between the return electrode 202A and the survey electrode 202C according to:

$$Z_{1-3} = \frac{V_{1-3}}{I_3} \tag{1}$$

where impedance $Z_{1-3}$ is a complex number that describes the resistance $R_{1-3}$ and capacitive reactance $X_{1-3}$ of the fluids and formation between those electrodes:

$$Z_{1-3} = R_{1-3} + jX_{1-3} \tag{2}$$

Impedance is frequency-dependent because the reactance term X is proportional to frequency, and impedance can include other terms (not shown in equation (2)) such as induced polarization terms and electrode geometry factors.

Control circuitry can measure any other potential difference, current, or other electrical parameter at the same or substantially the same time or at different times. Control circuitry can use measurements of fluid sensing component 200 taken over time, for example over a cement curing process, in order to monitor the cement curing process, or to monitor for possible breaches or deterioration of cement after the cement curing process.

Injection current $I_3$ flowing from the survey electrode 202C is injected into surrounding fluids to spread radially from the survey electrode 202C to a distance at least partially dependent on the frequency of the excitation signal, and returns at the return electrode 202A. Control circuitry can control injection currents and the potential at electrodes 202A-C to focus current deeper into fluids surrounding fluid sensing component 200, thus giving sensitivity for detection of materials or fluids, such as oil-based mud, which can be further away from electrodes 202A-C. A first and second focusing condition can be written as:

$$I_3 = 1 \tag{3}$$

$$V_2 - V_3 = 0 \tag{4}$$

where $I_3$ is the current at the survey electrode 202C, and $V_2$ and $V_3$ are voltage potentials measured at the focusing electrode 202B and the survey electrode 202C, respectively.

First focusing condition (3) illustrates that a current $I_3$ is injected by electrode 202C. Second focusing condition (4) signifies that the potential of the focusing electrode 202B is held constant and at the same potential as the survey electrode 202C. Because current only flows between electrodes if a potential difference exists between electrodes, no current should flow between electrodes 202B and 202C when second focusing condition (4) is satisfied. Current $I_3$ can thereby be permitted to flow further from fluid sensing component 200 into, for example, oil-based mud 212 to permit increased sensitivity of impedance measurements in the presence of oil-based mud.

Some embodiments may provide a plurality of sets of first and second focusing conditions, similar to focusing conditions (3)-(4), for a plurality of combinations of electrodes. Further, embodiments are not limited to three electrodes. The distance into the surrounding formation 214 that injection current $I_3$ can travel will depend on: (1) the frequency of the excitation signal, (2) the spacing between electrodes, and (3) the size of the electrodes, although other factors may also affect the propagation distance of injection current $I_3$.

Additional system equations for fluid sensing component 200 can be written as:

$$I_1 + I_2 + I_3 = 0 \quad (5)$$

$$I_1 + I_3 = 0 \quad (6)$$

where $I_1$, $I_2$, $I_3$ are the currents at each of electrodes 202A-C, respectively.

Equation (5) illustrates that the system is a closed system, i.e., no current is entering or leaving the system. Equation (6) signifies that only the return electrode 202A receives current $I_3$ injected by electrode 202C. In other words, the magnitude of currents $I_1$ and $I_3$ is the same, but flowing in opposite directions (i.e., the current is ejected out of electrode 202C and into electrode 202A).

By measuring an electrical parameter such as voltage $V_{1-3}$ oil-based mud or other substances can be detected, and voids or cracks (not shown in FIG. 2) in formation 214 can be detected, by calculating impedances as described with reference to Equations (1)-(2) and comparing those impedances to those expected or predicted for different substances.

Figure 3:
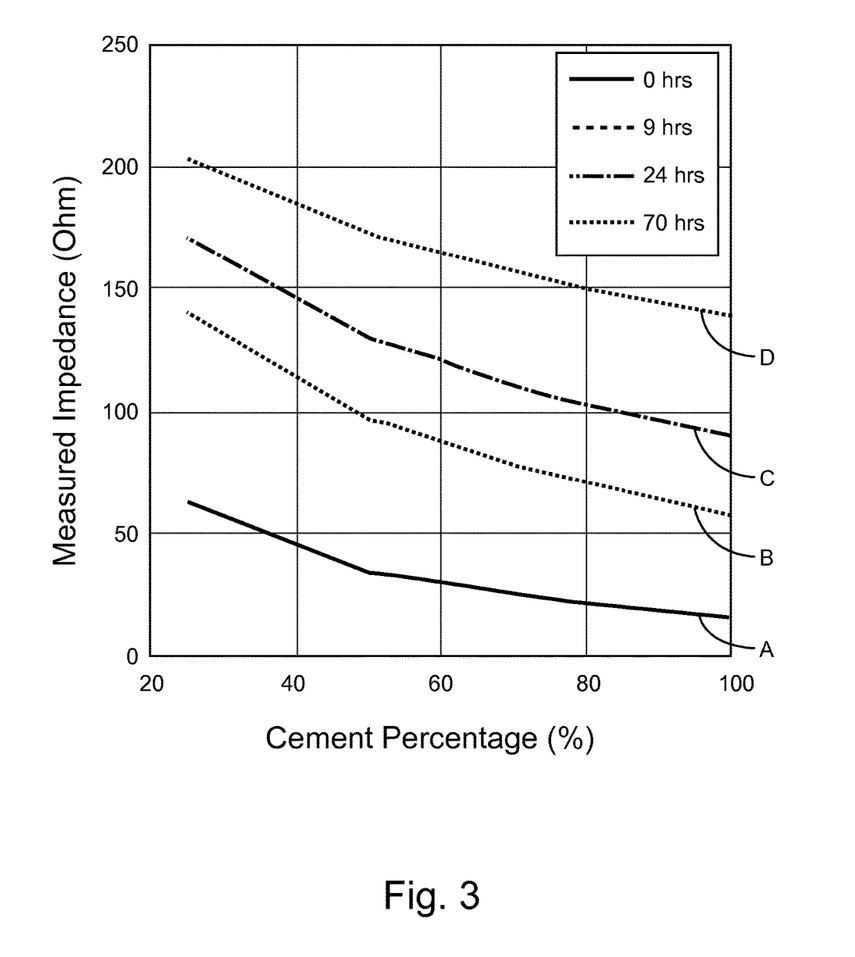
FIG. 3 illustrates impedances, as a function of percentage of cement in a mixture of cement and other substances, measured between electrodes of a fluid sensing component in accordance with some embodiments.

FIG. 3 illustrates impedances as a function of percentage of cement in a mixture of cement and other substances, measured between electrodes of a fluid sensing component 200 (FIG. 2) in accordance with some embodiments. The other substances can be oil-based mud, for example. Curve A illustrates the measured impedance at time of emplacement of cement, and curves B, C, and D illustrate measured impedance as a function of cement percentage at 9 hours, 24 hours, and 70 hours after emplacement, respectively.

Figure 4:
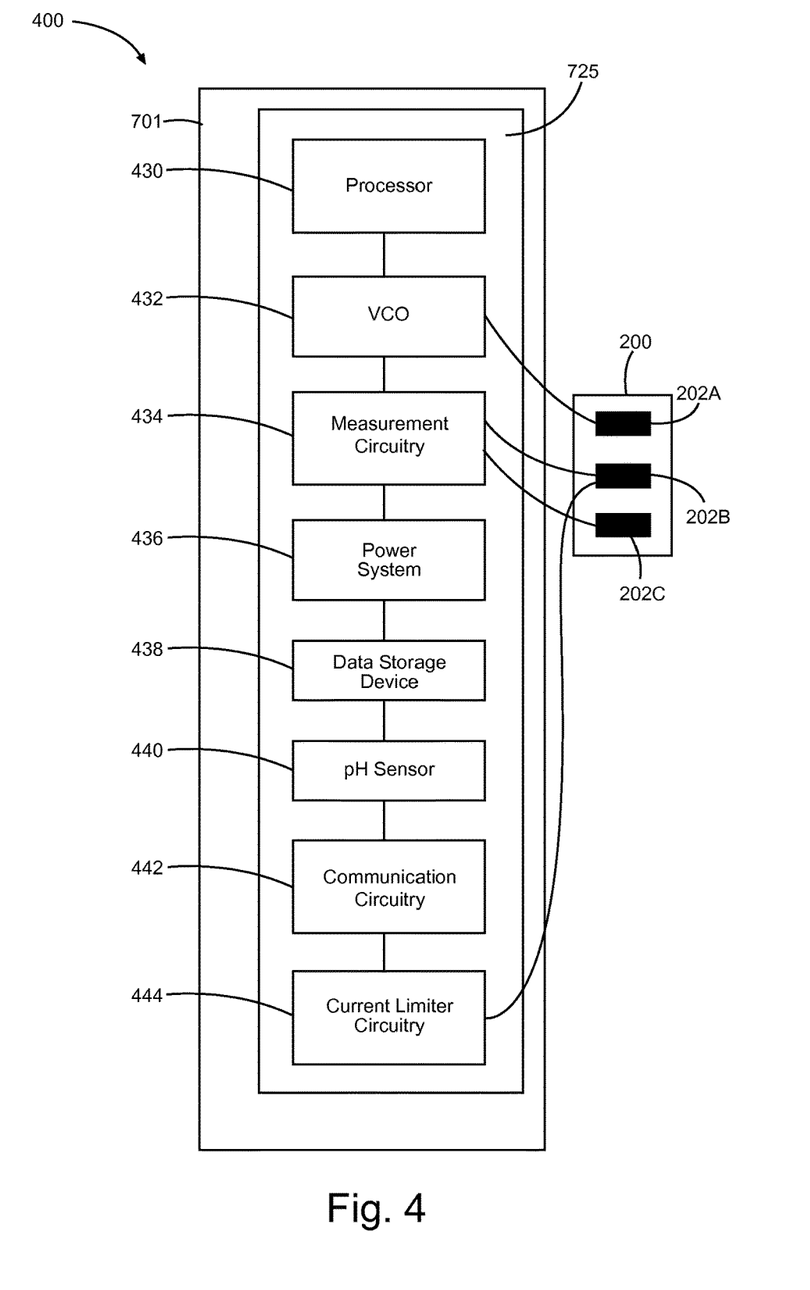
FIG. 4 depicts a schematic view of an example electronics assembly for performing functions of various embodiments.

FIG. 4 depicts a schematic view of an example electronics assembly 400 that will perform functions of various embodiments. Electronics assembly 400 enforces focusing conditions (3)-(4), and electronics assembly 400 measures voltages and currents to calculate impedances as described with reference to Equations (1)-(2).

In various embodiments, one or more components of electronics assembly 400 shown in FIG. 4 will be housed in rib 701 or tube 725 in a communication assembly (discussed later herein in reference to 700 in FIG. 7). In the depicted example of electronics assembly 400, the assembly includes one or more processors 430 and a variable signal generator to provide excitation to one or more of electrodes 202A-C. In this example, the variable signal generator is a voltage-controlled oscillator (VCO) 432; but other forms of generators may provide the excitation currents, such as a dedicated integrated circuit (IC) and related circuitry.

Measurement circuitry 434 couples to one or more of electrodes 202A-C to receive current resulting from passage of the excitation currents through the fluid and other materials in the well annulus 26.

Processor(s) 430 control the operation of VCO 432 and of measurement circuitry 434. Processor(s) 430 additionally process received signals, as described elsewhere herein, such as in reference to FIGS. 5 and 6. In some example systems, one or more processors may be dedicated to the functionality associated with measurement circuitry 434. Where electronics assembly 400 does all processing, each fluid-sensing component 200 will typically consist primarily of a plurality of electrodes in electrical communication with electronics assembly 400, with all other functionality provided by electronics assembly 400.

In some embodiments, a processor (430 in FIG. 4) will control circuitry to comply with first and second focusing conditions (3)-(4). Processor 430 can receive parameters or information relative to focusing conditions, sets of focusing conditions, or a plurality of sets of focusing conditions, to use at various times in a cementation process or other oil exploration and production process, from a surface system (38 in FIG. 1) or other system. Processor 430 can store focusing conditions in data storage device (438 in FIG. 4). In examples, processor 430 can store focusing conditions in data storage device 438 using a relational database to relate appropriate times for using each set of focusing conditions relative to an onset of a cementation process. Processor 430 can include or control current limiter circuitry 444 for implementing one or more focusing conditions.

In some embodiments, a processor (430 in FIG. 4) controls VCO 432 to provide the excitation signal according to first and second focusing conditions described earlier with reference to focusing conditions (3)-(4).

Any one or more processors 430 and/or measurement circuitry 434 will typically be coupled to data storage device 438 for either temporary or continued storage of instructions, data, etc. Other components of electronics assembly 400 can couple to data storage device 438 as desired for a specific implementation. Data storage device 438 may be any form of electrical storage mechanism, and in most examples will include one or more of volatile or nonvolatile memory, including one or more of DRAM, SRAM, Flash, MRAM, and combinations of any of the foregoing, as well as other known forms of memory devices. For purposes of the present disclosure, any such storage mechanism, whether volatile or nonvolatile memory shall be considered a non-transitory storage device (or memory).

Electronics assembly 400 also includes a power system 436 configured to supply power at least in the electronics assembly 400, and in many cases to the entire communication assembly (as discussed at 700, in FIG. 7), with which it is associated. In many examples, power system 436 will include one or more batteries. Processor 430 can control power system 436 to operate communication assembly for a time duration sufficient for monitoring fluids throughout, for example, a curing process. To provide enhanced power efficiencies, processor 430 can awaken communication assembly 700 from a sleep state based on, for example, a pH change detected by pH sensor 440.

Example electronics assembly 400 will often also include communication circuitry 442 to enable communication with an external location, as described elsewhere herein. Electronics assembly 400 can transmit, receive, process, and telemeter EM signals to a central processing unit located at the surfaces. Communication circuitry can include components for wired, wireless, optical, or any other type of communication.

Processor(s) 430 can determine or enforce first and second focusing conditions (3)-(4), or the focusing conditions may be determined or enforced by a surface system 38 (FIG. 1) or other system. In the latter case, surface system 38 transmits focusing conditions or data representative of focusing conditions to processor(s) 430. Software, hardware, firmware, or any combination thereof can apply focusing conditions by using a combination of voltages and currents each of which is obtained through unfocused measurements. Data storage device 438, memory of surface system 38, or memory of another system can store focusing conditions and data representative of focusing conditions.

Figure 5:
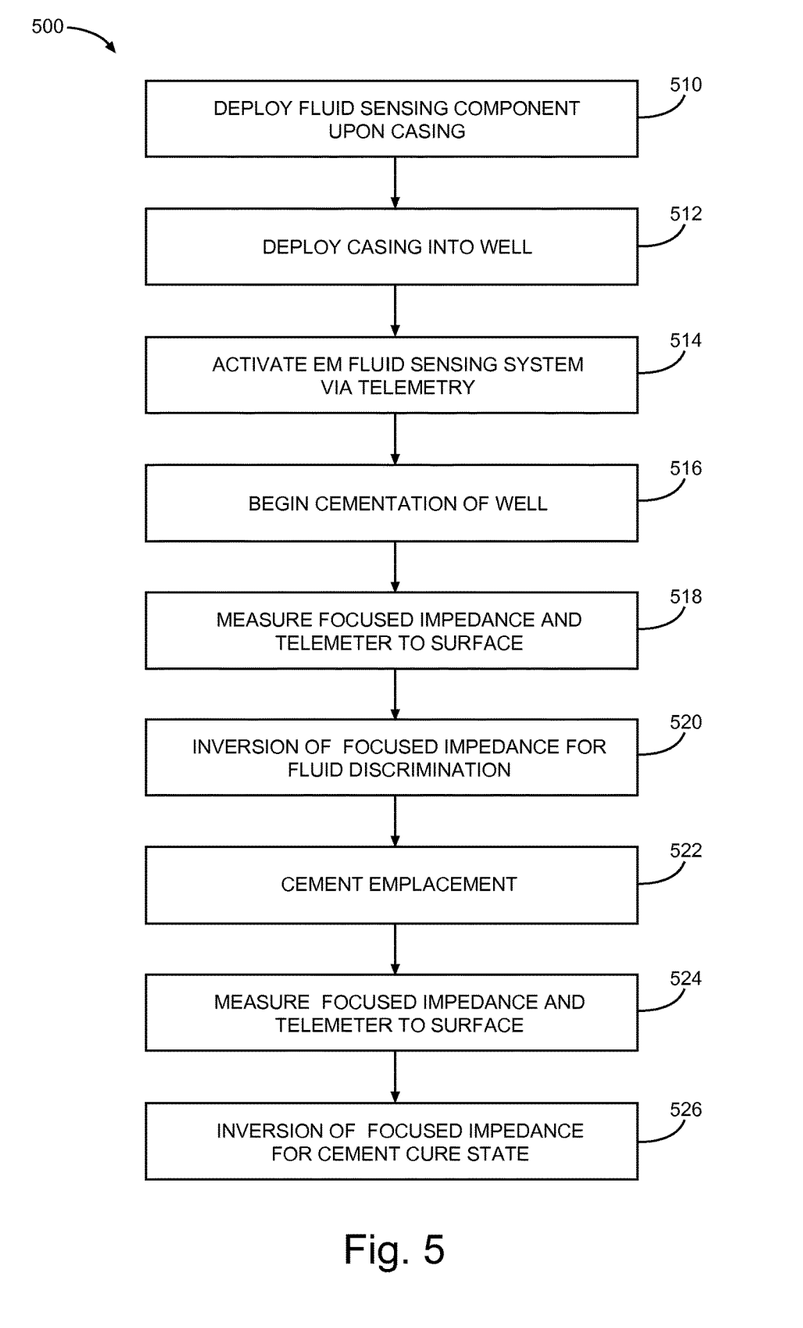
FIG. 5 depicts a flow chart of an example method for using electrodes of a fluid sensing component and components of an electronics assembly to perform impedance measurements in accordance with some embodiments.

FIG. 5 depicts a flow chart of an example method 500 for using electrodes 202A-C of fluid sensing component 200 (FIG. 2) and components of electronics assembly 400 to perform impedance measurements in accordance with some embodiments. Some operations of method 500 may be implemented by surface system 38 (FIG. 1), processor 430, measurement circuitry 434 or other circuitry included in electronics assembly 400 (FIG. 4) or by components such as communication components of communication assembly (as described at 700 in FIG. 7).

In operation 510, at least one fluid sensing component 200 is deployed on a casing 20. Fluid sensing component 200 can be deployed with a communication assembly or separately from a communication assembly (as described at 700 in FIG. 7).

In operation 512, casing 20 is deployed into a well. In operation 514, surface system 38 activates electronics assembly 400 to communicate with fluid sensing component 200 using telemetry, such as acoustic or fluid pulse, telemetry or by other communication through communication assembly 700. In some operations, surface system 38 activates electronics assembly 400 to some degree at or shortly before casing 20 is placed into the well, though in some example operations, electronics assembly 400 may be in a relatively low power state, and may later enter one or more relatively increased activity states. Entry to such increased activity states can occur after either passage of a prescribed period of time, or in response to some other stimuli, which could include a telemetered signal. In operation 516, cement is pumped downhole to begin a cementation process. The cement may be placed downhole as part of a primary cementing, secondary cementing, or other sealant operation.

In operation 518, measurement circuitry 434 measures voltage for use in determining focused impedance according to Equations (1)-(2). Processor 430 or circuitry on the communication assembly or other communication circuitry can telemeter the measurements to surface system 38. Measurement circuitry 434 determines impedances based on excitation signals generated according to FIG. 2 and Equations (1)-(2). Processor 430 or other circuitry can control voltages, excitation signals, or other signals, and which electrodes will receive or sense these voltages, excitation signals, and other signals, to generate different focused impedance data as described later herein in reference to an example method of making measurements in a well (FIG. 6 at 600), but other methods can be used.

In operation 520, the surface system 38 can perform inversion of the impedance for fluid discrimination. For example, a processor (430), which may be either downhole or in a surface system 38, can determine fluid identities according to the predicted or estimated fluid electrical properties that have been predicted or estimated based on physical measurements, e.g., at the well site, or in a laboratory. For example, processor 430 or the surface system can access or retrieve data from a lookup table that defines fluid types of fluids within the annulus based on characteristics of signals received at the electrodes 202A-C, wherein the lookup table was previously generated based on laboratory measurements or field experiments, etc. By comparing obtained impedances with these predicted or estimated fluid electrical properties, processor 430 can detect presence (or absence) of a particular fluid to identify what fluids are present at the location of the electrodes, which may monitor, for example, of the cementing operation (for example, to determine the TOC). In some embodiments, processor 430 can configure a telemetry message that includes measurement data to a surface system, and the surface system can perform fluid discriminating functionalities to determine such fluid identities.

After cement emplacement 522, the example method can, in many examples, continue to measure voltages to determine impedance in annulus 26, as indicated at 524. In many examples, the measurements and/or the determined impedances will be telemetered to surface system 38, which may be done essentially in real time or at selected intervals. Surface system 38 can use these measurements, after placement of the cement, to identify the cure state of the cement, and also during cure or at later intervals to identify any fluid incursion of the cement barrier. As described previously, these measurements can be made in the same manner as previously described through reference to FIG. 6, or by other desired methods. In examples in which the impedances are either not determined the downhole or are not implemented to determine a cement cure state downhole, such operations can be performed at the surface, for example by surface system 38, as indicated at operation 526.

In performing the described method, the frequencies to be used to obtain current measurements at various times can be determined prior to the operation, or in other alternatives, can be communicated from surface system 38 or other system, or can be determined by a downhole processor (430 in FIG. 4). Frequencies to be used for excitation signals of method will, in many examples the based on actual or expected properties of surrounding fluids. In examples of the described method, surface system 38 can receive measurements from the communication assembly over a variety of time intervals and display layer boundaries, or another fluid parameter, as a function of time or frequency.

In some embodiments, processor 430, surface system 38, or another system can model, invert, or provide display of the measured impedances to generate resistivity data of the materials filling annulus 26 between casing 20 and formation 14. In some embodiments, processor 430, surface system 38, or another system can model, invert or provide display of the measured impedances acquired to generate effective medium models of the materials filling annulus 26 between casing 20 and formation 14. These effective medium models can functionally describe measured impedances in terms of physical properties such as fluid, grain size, etc. In various embodiments, surface system 38 can apply methods of model parameterization and regularization to enhance this inversion or imaging.

In some example systems, the method may also be used to identify properties of formations 14 defining wellbore 18 in addition to, or in some examples instead of, properties of materials in annulus 26. In such methods, generation of excitation currents of a magnitude and frequency as to result in the current traversing a portion of formation 14 to reach a return electrode can be received and used to predict, calculate, or estimate formation 14 resistivity in the proximity of the survey and return electrodes. In some cases, these determinations of formation 14 resistivity can be at least in part based upon or correlated with well logs acquired from open-hole wireline or logging-while-drilling (LWD) instruments. Surface system 38 can perform multiple deterministic-based inversions or stochastic-based inversions and subsequent post-inversion analyses that span different initial models, constraints, and regularization to quantify model uncertainty.

Figure 6:
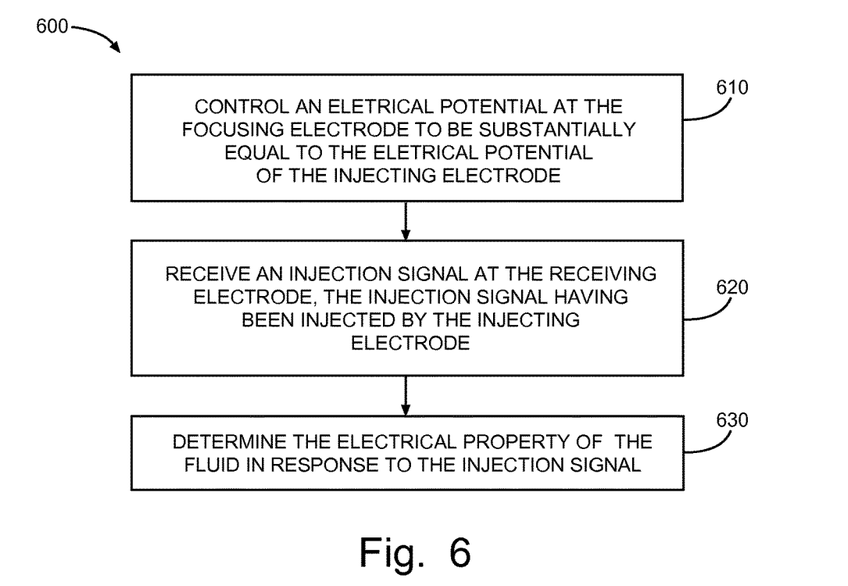
FIG. 6 depicts a flow chart of an example method of making focused impedance measurements in accordance with some embodiments.

Referring now to FIG. 6, that figure depicts a flow diagram of an example method 600 of making measurements in a well in accordance with some embodiments for implementing operation 518 of FIG. 5, as discussed above. For example, method 600 can determine fluid properties using excitation signals provided to one or more electrodes 202A-C.

In operation 610, processor 430 controls the electrical potential of electrodes 202A-C to maintain electrical potential at the focusing electrode 202B to comply with Equation (5) described earlier herein.

Method 600 continues at block 620 with receiving the injection signal at the return electrode 202A (FIG. 2). The injection signal will have been injected into surrounding fluids (210 and/or 212 in FIG. 2) and/or into the surrounding formation (214 in FIG. 2) by the survey electrode 202C (FIG. 2). The received injection signal will vary in response to the excitation signal and the properties of the path taken by the excitation signal to reach the return electrode. For example, the amplitude of the signal will typically vary in response to the frequency of the excitation signal. The amplitude of the signal can also vary in response to the difference in potential between the return electrode 202A and the survey electrode 202C. Further, the amplitude of the signal can vary in response to the distance of return electrode 202A from the survey electrode 202C. Measurement circuitry (434 in FIG. 4) measures voltage and current at the return electrode 202A, and provides these measurements to a processor (430 in FIG. 4).

In some embodiments, processor 430 can receive additional sets of focusing conditions, in series at various time instants or all in a single time instant. In other embodiments, processor 430 can retrieve sets of focusing conditions stored in data storage device 438. The sets can be similar in nature to first and second focusing conditions described earlier with reference to focusing conditions (3)-(4). Processor 430 can use the series of sets of focusing conditions to control the VCO 432 to provide additional excitation signals. In some examples, focusing conditions can specify that VCO 432 provide an excitation signal to a first electrode at one time instant and to a different electrode at a second time instant. VCO 432 can provide each excitation signal at different frequencies. However, embodiments are not limited thereto and VCO 432 can provide each excitation signal at the same frequency. Injection current will radiate a distance into the proximate fluid based on the frequency of the excitation signal. However, depending on the controlled electrical potential at other electrodes, the injection current may or may not be received at a particular other electrode. VCO 432 may sequentially apply each of these excitation signals based on the series of focusing conditions, as well as additional excitation signals at other frequencies, and different electrodes and can sense resulting currents based on electrical potential controlled by the processor 430 at each of those electrodes in accordance with the series of focusing conditions.

Processor 430 can select which set of focusing conditions to use based on criteria such as the amount of time that has elapsed since an onset of a wellbore cementation process. Processor 430 will control VCO 432 to provide excitation signals according to the selected focusing condition, and processor 430 will further control electric potential at electrodes 202A-C based on the selected set.

Method 600 continues at block 630 with determining a property of a fluid within annulus 26 in response to the received injection signal. For example, processor 430 can determine fluid identities as described herein. In other example, another processor, for example in surface equipment, can receive the measurements, either has received or after some processing, and can be used to determine the fluid identities. In systems configured to provide excitation currents that will traverse the formations surrounding the wellbore, surface system 38 can evaluate the return current in reference to formation models to provide a measure of formation properties such as resistivity and/or permeability, and in some cases porosity.

Figure 7:
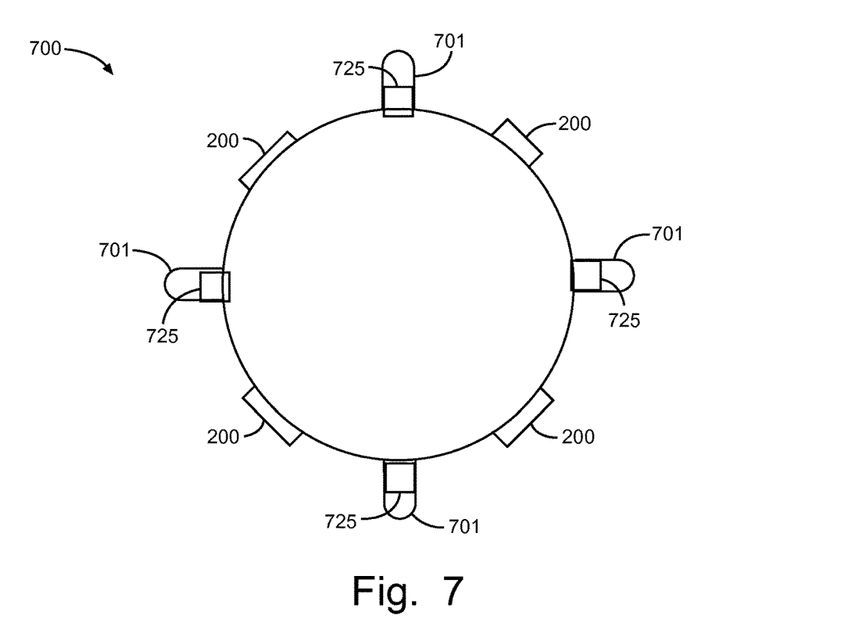
FIG. 7 depicts a cross-sectional schematic view of an example communication assembly as may be used to measure the sealant (or other well servicing fluids) present within different azimuthal regions of the annulus or to measure resistivity, ion concentration, acidity, or other properties of fluids proximate communication assembly in accordance with some embodiments.

FIG. 7 is a cross-sectional schematic view of an example communication assembly 700 on which fluid sensing components 200 and other components can be mounted to measure the sealant (or other well servicing fluids) present within different azimuthal regions of the annulus; or to measure or determine impedance, ion concentration, acidity, or other properties of fluids proximate communication assembly 700 in accordance with some embodiments. Communication assembly 700 is discussed below with reference to some elements depicted in FIGS. 2 and 4.

Example communication assembly 700 includes a plurality of ribs 701 that extend longitudinally along communication assembly 700 and in spaced relation to one another around the periphery of communication assembly 700. Example communication assembly 700 includes four ribs 701 generally equally spaced around communication assembly 700, and therefore generally equally spaced relative to the circumference of casing 20. As will be apparent to persons skilled in the art having the benefit of this disclosure, either a greater or a lesser number of ribs 701 can be utilized according to needs of a particular application.

In communication assembly 700, ribs 701 are hollow, and house control circuitry and/or other electronics (400 in FIG. 4), as well as additional circuitry to enable communications with an external location, etc. In many examples, ribs 701 will be of a geometric shape that reduces or eliminates the effect of ribs 701 on flow of fluids past or near ribs 701. In many examples, ribs 701 will encircle or enclose a tube 725 or similar structure configured to house and protect control circuitry and other electronics therein from pressure, abrasion, etc. Such tubes 725 or other structures can be include a suitable metal, such as steel, or another material suitable for the specific application, as will be apparent to persons skilled in the art having the benefit of this disclosure.

In various embodiments, communication assembly 700 includes fluid sensing components 200. As described herein with reference to FIGS. 2, 5 and 6 and Equations (1)-(2), electrodes of fluid sensing components 200 can receive an excitation signal causing electrodes to inject injection currents into annulus 26. The injection currents can traverse the adjacent dielectric environment (i.e., the adjacent fluid) to reach one or more additional electrodes of fluid sensing components 200.

In the depicted schematic representation, a fluid sensing component 200 is provided between each pair of adjacent ribs 701, such that a fluid sensing component 200 is angularly offset from an adjacent fluid sensing component 200, to provide impedance measurements that vary with properties of fluids passing by communication assembly 700 in the well annulus 26. In other systems, a communication assembly may only include a single fluid sensing component 200 proximate a given depth.

Depending on the number of fluid sensing components 200 mounted to assembly 700, fluid sensing components 200 can be angularly offset from each other by a number of angular degrees, for example by about ninety degrees, about sixty degrees, etc. In the depicted example, fluid sensing components 200 are presumed to be configured such that all electrodes of fluid sensing components 200 are placed between ribs 701. However, embodiments are not limited thereto and at least one electrode of a fluid sensing component 200 can be mounted on a rib 701 or in other configurations (as described below referring to FIGS. 8 and 9A-G). Further, in some embodiments, a fluid sensing component 200 can be provided between one pair of adjacent ribs 701, while a fluid sensing component 200 may not be provided between another (or any other) pair of adjacent ribs 701.

In some configurations, fluid sensing components 200 can provide azimuthal information by detecting generally within a determined azimuthal region of annulus 26. In some implementations, these azimuthal regions may all be distinguished from one another, while in others the azimuthal regions may partially overlap with one another. The presence of overlap, or the degree of an overlap, if any, may depend on the number and placement of fluid sensing components 200. Any number of ribs, tubes, or corresponding structures, may be provided as necessary to house the necessary circuitry, and as desired to provide detection within a determined azimuthal region surrounding communication assembly 700 or to provide signaling and related processing for fluid sensing components 200.

The various electronic circuits within each rib 701 can communicate as desired with circuitry in another rib 701. Such communications between can occur through use of any suitable mechanism as will be apparent to those skilled in the art, for example, through use of a serial peripheral interface (SPI), though embodiments are not limited thereto.

Communication assembly 700 can associate with casing 20 by a variety of mechanisms. Each communication assembly includes a body member 718 supporting other components and facilitating association with casing 20.

Figure 8:
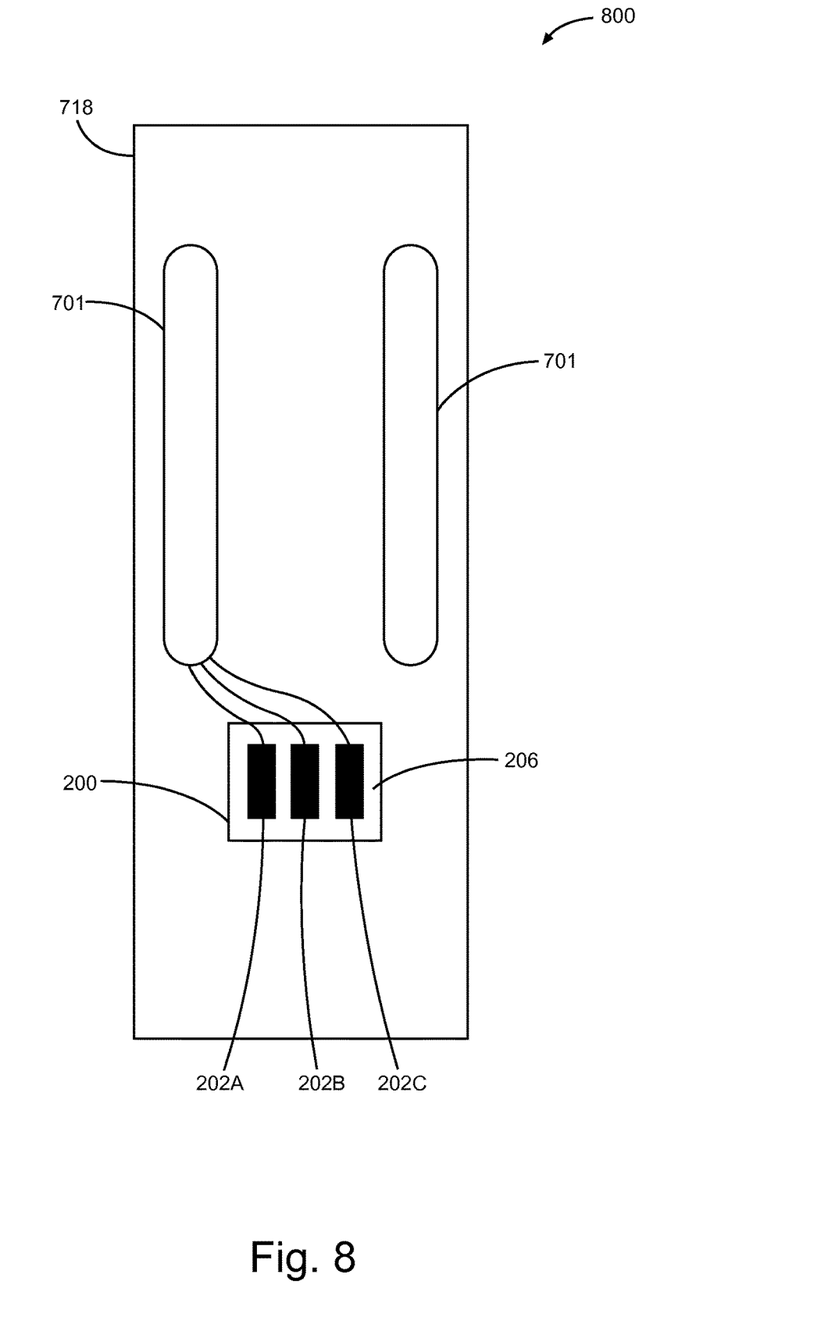
FIG. 8 depicts a side view of an example communication assembly in accordance with some embodiments.

FIG. 8 depicts a side view of a communication assembly 800 in accordance with some embodiments. Components comparable to those discussed relative to FIG. 7 are numbered similarly in FIG. 8.

Fluid sensing component 200 includes a plurality of electrodes 202A-C. Electrodes 202A, 202B, 202C will be referred to as belonging to a fluid sensing component 200 when one of the electrodes 202A-C provides injection current received at another of the electrodes 202A-C.

While FIG. 8 characterizes a system having three electrodes, other configurations may be used. Depending upon the specific materials of construction of various portions of a respective communication assembly, electrodes 202A-C may be secured proximate a metallic surface, such as by being mounted on an insulating base 206 to prevent electrical shorts against such metallic surface of the communication assemblies.

In the depicted example, communication assembly 800 includes a plurality of electrodes 202A-C arranged to provide a fluid sensing component 200. Though only one side of communication assembly 800 is shown, it should be understood that the described fluid sensing component 200 might be replicated at a plurality of azimuthally offset locations around communication assembly 800. Therefore, any fluid sensing component 200 can sense fluid properties within an overlapping or non-overlapping azimuthal range of other fluid sensing components 200 around communication assembly 800.

Electrodes 202A-C will be spaced at intervals such that injection currents injected by one electrode 202A-C will traverse different distances to reach the other electrodes 202A-C. Persons skilled in the art having the benefit of this disclosure with recognize that the longer the spacing between an electrode 202A-C injecting an injection current and an electrode 202A-C configured to receive the injection current after the injection current has traversed the surrounding dielectric environment, the greater the distance the signal will extend into that environment. This effect can be further promoted with guard electrodes placed between the survey and return electrodes, as known to persons skilled in the art. Additionally the longer distance allows the signals to better reflect the effects of that dielectric environment. In applications in which these effects are desired, the electrodes can be longitudinally spaced, one of above the other, along the communication assembly 700.

The relative placement, geometric configuration, and other design parameters of electrodes 202A-C can be adjusted to improve the likelihood of detection of changes in the electrical environment resulting from changes in the surrounding fluids. For example, the electrodes 202A-C can be positioned nearer to each other for greater sensitivity to changes nearer to fluid sensing component 200. Conversely, electrodes 202A-C can be positioned further away from each other for greater sensitivity to changes further away from fluid sensing component 200.

Electrodes 202A-C can be placed on insulating base 206 in various shapes, such as conductive strips, concentric loops etc. Each electrode 202A-C can be in the form of a solid component (for example, metal plates or strips) secured to insulating base 206, or, in other examples, can be formed of a coating metallized, or otherwise deposited, onto insulating base 206. Electrodes 202A-C can extend longitudinally along the assembly or laterally around the communication assembly, as described below in reference to FIGS. 8 and 9A-G.

In some embodiments, electrodes 202A-C can be spaced from each other in a symmetrical arrangement, for example, electrode 202A can be spaced at about a same distance from electrode 202B as electrode 202C is spaced from electrode 202B. In other embodiments, electrodes 202A-C can be spaced asymmetrically from each other. For example, electrode 202A can be spaced about ½ inch from electrode 202B and electrode 202B can be spaced about one inch from electrode 202C. Embodiments are not limited to any particular spacing, however. Operators can determine appropriate electrode spacing to provide comparative measurements of impedance at various distances from a communication assembly. Electrode spacing can also be determined based on, for example, power requirements, expected types of substances and fluids downhole, and surface areas of electrodes 202A-C, among other factors.

FIGS. 9A-9G illustrate additional alternative configurations of for mounting fluid sensing component 200 onto casing 20. For clarity of illustration, only fluid sensing components 200 with electrodes 202 are shown as mounted to casing 20. However, it will be understood that other components, for example ribs, electronics assemblies, etc., can additionally be mounted on casing 20 in accordance with some embodiments.

Figure 9A:
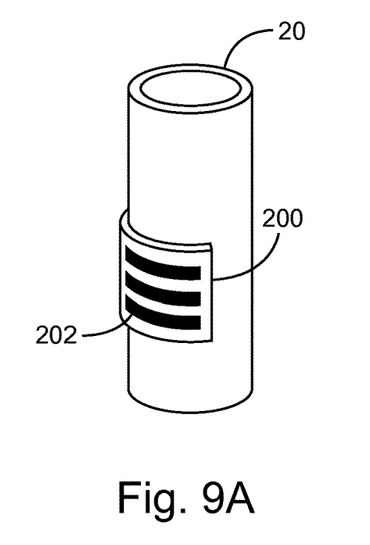
FIGS. 9A-G each depicts a respective alternative example arrangement of a plurality of electrodes supported at the exterior of a casing string.
Figure 9B:
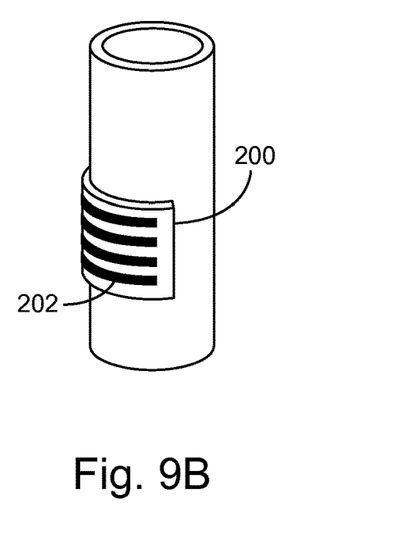
Figure 9C:
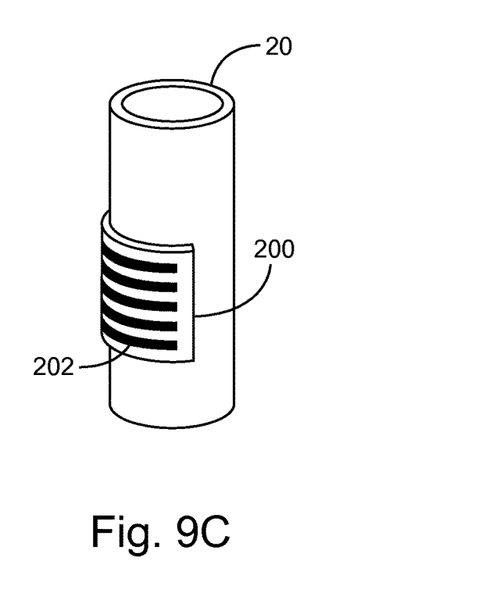
Figure 9D:
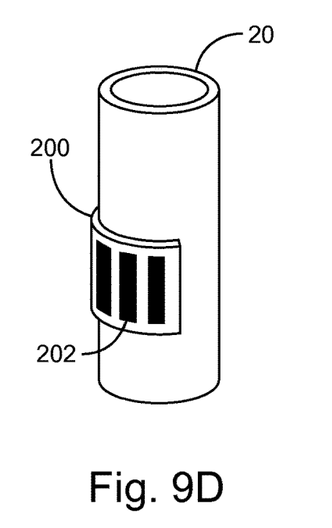
Figure 9E:
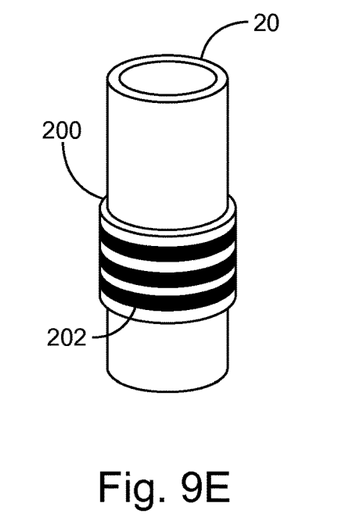
Figure 9F:
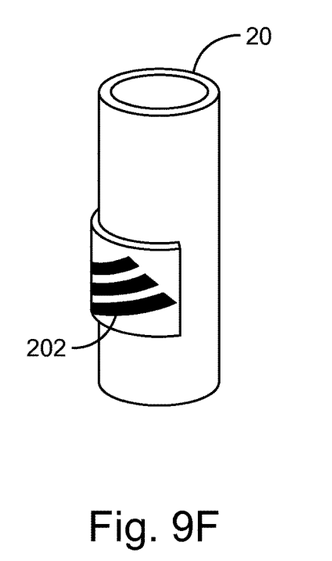

Referring to FIG. 9A, electrodes 202 can be of finite length and aligned perpendicular to the casing 20 axis. Fluid sensing component 200 is not limited to including three electrodes. On the contrary, fluid sensing component 200 can include four electrodes (FIG. 9B), five electrodes (FIG. 9C), or any other number of electrodes 202 greater than or equal to two electrodes.

Figure 9G:
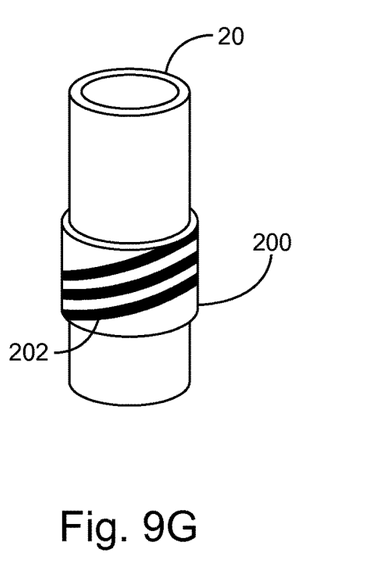

Further, fluid-sensing component 200 is not limited to any particular alignment of electrodes 202. On the contrary, electrodes 202 can be of a finite length and width, and aligned parallel to the casing axis (FIG. 9D), encircling the casing and aligned perpendicular to the casing axis (FIG. 9E), of finite length and aligned at an angle with respect to the casing axis (FIG. 9F), or encircling the casing and aligned at an angle with respect to the casing axis (FIG. 9G). However, embodiments are not limited to the illustrated arrangements of electrodes 202 and the electrodes 202 can have any other arrangement or alignment.

As is apparent from the discussion above, in many example systems, a plurality of communication assemblies will be disposed in longitudinally spaced relation to each other along the casing 20, at least over a region of interest relative to either the sealing operation or to other downhole conditions. Accordingly, by sensing fluids of a certain type in response to impedance values determined in accordance with FIG. 2 and Equations (1)-(2), a location, in particular TOC, can be determined by finding a location on casing 20 where below it, impedance values associated with the sealant are identified, while above the location, only impedance values associated with other fluids, for example spacer fluid or drilling mud, are identified. Furthermore, monitoring of quality of barrier, and fluid discrimination can be performed using apparatuses and methods in accordance with some embodiments.

Each communication assembly will preferably include an azimuthal indicator, for example a compass, to determine the orientation of the communication assembly once it is disposed within the borehole. With a known orientation of the communication assembly, the orientation of each rib or fluid sensing component 200 will be known and therefore the quadrant or other azimuthally offset region being investigated will similarly be known. The depth of each casing assembly can be known, for example through a record of the location of each communication assembly as it is associated with casing 20 as casing 20 is placed in the wellbore, providing a measure of depth as to the surface.

In different examples, TOC measurement can be done after the pumping of the sealant is completed or the measurement can be a dynamic measurement of the TOC while the sealant is moving up annulus 26. The other measurements described herein facilitate measurements not only of the TOC, but also of the distribution of the cement or other sealant around casing 20 over the region of the casing string that includes associated communication assemblies. Identifying both the depth and orientation where this occurs facilitates remediation efforts.

Each communication assembly 700 can report information associated with the fluid sensing components to a surface system, for example surface system 38, using communication methods known to those of ordinary skill in the art having benefit of this disclosure. In some examples, this may be as basic as a potential difference measurement associated with electrodes of a fluid sensing component, grouped, or formatted in a manner to indicate the azimuthal orientation of the sensing.

The novel techniques described above can determine properties of sealant (or another fluid in the borehole) by processing impedance measurements or other measurements taken by an electrode-based fluid-sensing component. As discussed earlier, signals, for example oscillating signals, can excite electrodes of the fluid sensing component. Processors or other associated electrical systems can enhance the sensitivity of the fluid sensing component by controlling which electrodes of the fluid sensing component will inject current into fluids, and by controlling which electrodes of the fluid sensing component will sense these injected currents by maintaining particular potential differences between various electrodes.

In summary, using the apparatus, systems, and methods disclosed herein can provide azimuthally oriented indications of various properties or conditions downhole, and in particular can provide information regarding the top of cement and the quality of the barrier in of the annulus azimuthal regions. Properties of the fluid can similarly be monitored azimuthally, by taking impedance measurements based on impedances sensed by electrode-based fluid sensing components to infer dielectric properties of fluids.

The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Although specific embodiments have been illustrated and described herein, it should be appreciated that any arrangement configured to achieve the same purpose may be substituted for the specific embodiments shown. This disclosure is intended to cover any and all adaptations or variations of various embodiments. Combinations of the above embodiments, and other embodiments not described herein, will be apparent to those of skill in the art upon reviewing the above description.

What is claimed is:

1. An assembly for use with a casing string in a borehole through a subterranean formation, comprising:
    a body member disposed on the exterior of the casing string to be placed in the borehole, wherein an annulus is defined between the body member and the subterranean formation;
    a first fluid sensing component supported by the body member, the first fluid sensing component including a plurality of electrodes, the plurality of electrodes including at least one survey electrode, at least one return electrode, and at least one focusing electrode, the focusing electrode being between the survey electrode and the return electrode, the first fluid sensing component being arranged to sense an electrical impedance between the survey electrode and the return electrode, wherein the electrical impedance varies based on properties of a material in the annulus; and
    an electronics assembly supported by the body member and operably coupled to the first fluid sensing component, including, a signal generator to provide an excitation current to the survey electrode, circuitry to control electrical potentials at the survey electrode and the focusing electrode such that current is inhibited from flowing between the at least one survey electrode and the focusing electrode, measurement circuitry to measure currents resulting from the excitation current that has traversed the material proximate the first sensing component, and current limiter circuitry, to limit current injected by the focusing electrode.

2. The assembly of claim 1, wherein the assembly further comprises:

a data storage device configured to store measurements obtained by the measurement circuitry.

3. The assembly of claim 1, wherein the plurality of electrodes are arranged in conductive strips on a dielectric material.

4. The assembly of claim 3, wherein the plurality of electrodes extend longitudinally along a length of the assembly.

5. The assembly of claim 3, wherein an electrically insulating material is disposed over at least a portion of the plurality of electrodes.

6. The assembly of claim 3, wherein the at least one focusing electrode is spaced a first distance from the survey electrode and wherein the at least one focusing electrode is spaced a second distance from the return electrode.

7. The assembly of claim 6, wherein the first distance is different from the second distance.

8. The assembly of claim 1, wherein the assembly further comprises:
a second fluid sensing component supported by the body member and angularly offset from the first fluid sensing component on the body member, the second fluid sensing component including a plurality of electrodes and being configured to sense an electrical impedance between one or more pairs of electrodes of the plurality of electrodes, and wherein the electrical impedance varies based on properties of a fluid in the annulus, and
wherein as a result of the angular offset of the second fluid sensing component relative to the first fluid sensing component, the first and second fluid sensing components are sensitive to fluid conditions at first and second azimuthally offset regions of the annulus.

9. The assembly of claim 1, wherein the electronics assembly further includes a pH sensor.

10. A system for use in a borehole through a subterranean formation, comprising:
a casing string comprising first and second communication assemblies supported on the exterior of the casing string in an annulus and disposed in longitudinally spaced relation to one another along the casing string, wherein the annulus is defined between the casing string and the subterranean formation and wherein each communication assembly comprises,
a plurality of electrodes including at least one survey electrode, at least one return electrode, and at least one focusing electrode, the signal generator coupled to the survey electrode,
circuitry to control electrical potentials at the survey electrode and the focusing electrode such that current is inhibited from flowing between the survey electrode and the focusing electrode,
measurement circuitry to receive currents resulting from the excitation current that has traversed a material in the annulus, and
current limiter circuitry, to limit current injected by the focusing electrode.

11. The system of claim 10, wherein each of the at least one of the communication assemblies further comprises:
communication circuitry to obtain, from a surface system or other communication assembly, data representative of focusing conditions for use in controlling electrical potentials and for controlling the current limiter circuitry.

12. The system of claim 11, wherein the communication circuitry includes components for wireless communication.

13. The system of claim 11, wherein the communication circuitry includes components for optical communication.

14. The system of claim 11, further comprising a data storage device to store the data representative of the focusing conditions.

15. The system of claim 10, wherein at least one of the communication assemblies includes a plurality of fluid sensing components, each fluid sensing component including a portion of the plurality of the electrodes, and each fluid sensing component arranged on the communication assembly to obtain information associated with a fluid property within a selected azimuthal region of the annulus.

16. A method of making measurements in a borehole through a subterranean formation, comprising:
associating a sensor assembly with the exterior of a casing string being placed in the borehole, the sensor assembly configured to sense an electrical property of a fluid in an annulus surrounding the casing string between the casing string and the formation, the sensor assembly including at least one survey electrode, at least one return electrode, and at least one focusing electrode in spaced relation to one another and the focusing electrode being spaced between the survey electrode and the return electrode;
providing an excitation signal to the survey electrode;
controlling an electrical potential at the focusing electrode to be substantially equal to the electrical potential of the survey electrode;
receiving an injection signal at the return electrode, the injection signal having been injected by the survey electrode; and
determining the electrical property of the fluid in response to the injection signal.

17. The method of claim 16, wherein
a first focusing condition is defined to specify the electrode of the plurality of electrodes to which the excitation signal is to be provided,
a second focusing condition is defined to specify the electrical potential at the focusing electrode, and
the method further comprises receiving data representative of the first focusing condition and the second focusing condition from a surface system.

18. The method of claim 17, further comprising:
receiving data representative of a plurality of first focusing conditions; and
providing a series of excitation signals to an electrode selected from the group consisting of the at least one survey electrode, the at least one return electrode, and the at least one focusing electrode based on the plurality of first focusing conditions, wherein at least one of the series of excitation signals is provided to a different electrode than at least one other of the series of excitation signals.

19. The method of claim 18, further comprising:
selecting a set including a first focusing condition and a second focusing condition from the series of first focusing conditions and second focusing conditions, based on an amount of time that has elapsed since an onset of a wellbore cementation process, to generate a selected set; and
providing the excitation signal and controlling electrical potential based on the selected set.

20. The method of claim 16, further comprising:
storing a value representative of the electrical property; and
generating a message that includes the value if the value is outside an expected range.

* * * * *